United States Patent [19]

Keil et al.

[11] Patent Number: 5,557,013

[45] Date of Patent: Sep. 17, 1996

[54] PREPARATION OF O-SUBSTITUTED HYDROXYLAMMONIUM SALTS

[75] Inventors: Michael Keil, Freinsheim; Josef Wahl, Schifferstadt; Ulrich Klein, Limburgerhof; Wolfgang Will, Kirchheim, all of Germany

[73] Assignee: BASF Aktiengesellschaft, Ludwigshafen, Germany

[21] Appl. No.: 545,227

[22] Filed: Oct. 19, 1995

[30] Foreign Application Priority Data

Oct. 22, 1994 [DE] Germany .............. 44 37 905.6

[51] Int. Cl.$^6$ ..................................................... C07C 209/00
[52] U.S. Cl. ................................................................ 564/301
[58] Field of Search ..................................................... 564/301

[56] References Cited

U.S. PATENT DOCUMENTS

| | | | |
|---|---|---|---|
| 4,917,162 | 4/1990 | DeLongcamp | 152/5 |
| 5,382,685 | 1/1995 | Klein et al. | 564/301 |
| 5,488,162 | 1/1996 | Buckland | 564/301 |

FOREIGN PATENT DOCUMENTS

| | | |
|---|---|---|
| 1296022 | 2/1992 | Canada . |
| 23460 | 2/1981 | European Pat. Off. . |
| 23560 | 2/1981 | European Pat. Off. . |
| 121701 | 10/1984 | European Pat. Off. . |
| 158150 | 10/1985 | European Pat. Off. . |
| 158159 | 10/1985 | European Pat. Off. . |
| 259805 | 3/1988 | European Pat. Off. . |
| 591798 | 4/1994 | European Pat. Off. . |

OTHER PUBLICATIONS

Methoden der Organ. Chem. vol. 10/1, 4th Ed. 1971, p. 1181 ff.

Primary Examiner—Peter O'Sullivan
Attorney, Agent, or Firm—Keil & Weinkauf

[57] ABSTRACT

Preparation of O-substituted hydroxylammonium salts of the formula I

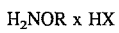

$$H_2NOR \times HX \qquad I$$

where R is a $C_1$-$C_6$-alkyl or $C_2$-$C_6$-alkenyl radical, each of which may be halogen-substituted, and X is chlorine or bromine, by reacting in an integrated process, without isolation of intermediates a) acetone with hydroxylammonium sulfate and sodium hydroxide solution to give acetone oxime;

b) treating the solution of acetone oxime thus obtained with sodium hydroxide solution and completely removing water, c) reacting the suspension of the acetone oxime Na salt thus obtained with alkylating agents at from 0.5 to 15 bar and at up to 140° C. to give acetone oxime ethers; and d) cleaving the acetone oxime ethers with acids HX to give the products I, a homogeneous, nonpolar aprotic solvent being used in all process steps a) to d).

7 Claims, No Drawings

PREPARATION OF O-SUBSTITUTED HYDROXYLAMMONIUM SALTS

The present invention relates to a process for preparing O-substituted hydroxylammonium salts of the formula I $$H_2NOR \times HX \qquad \qquad I$$

where R is a $C_1$-$C_6$-alkyl or $C_2$-$C_6$-alkenyl radical, each of which may be halogen-substituted, and X is chlorine or bromine.

The compounds I are useful intermediates for preparing pharmaceutical and crop protection active compounds. Such active compounds are described, for example, in EP-A 253 213.

The preparation of hydroxylammonium salts by means of individual steps is known in principle. After linkage of hydroxylamine to a protective group A, hydroxylamines doubly substituted on the N are obtained. These are then electrophilically substituted on the oxygen atom and in a third step cleaved with mineral acids with liberation of the protective group radical to give the compounds I:

$$H_2NOH \longrightarrow A=NOH$$

$$A=NOH + RY \longrightarrow A=NOR'$$

$$A=NOR + HX \longrightarrow H_2NOr' \times HX$$

(R'=eg. alkyl, X and Y=eg. Cl or Br)

The individual steps are described with the aid of examples, inter alia, in Houben-Weyl, Methoden der Organ. Chem. [Methods of Organic Chem.], Vol. 10/1, 4th Edition, 1971, page 1181 ff and Vol. 10/4, 4th Edition, 1968, page 55 ff. Thus the protective group A can be, for example, a phthaloyl radical, two sulfonate radicals or a 2-propylidene radical. The preparation of acetone oxime according to the first process step is cited, for example, in Houben-Weyl, Vol. 10/4, p. 58 and is carried out in aqueous medium. The alkylation of acetone oxime is described, for example, in Houben-Weyl, Vol. 10/4, p. 220 ff., and also in EP-A 23 460, EP-A 121 701 and EP-A 158 150.

An undesired secondary reaction under these reaction conditions in this case is N-methylation, which leads to nitrones and thus substantially decreases the yields of O-substituted products (Houben-Weyl, Vol. 10/4, p. 220).

The cleavage of acetone oxime methyl ether with mineral acids is described, for example, in Houben-Weyl, Vol. 10/1, p. 1186 ff. The reaction only takes place in satisfactory yields, however, if acetone is extracted from the equilibrium by distillation (EP-A 259 850, EP-A 591 798).

The conversion of the three individual steps described to an economical process in the production of large amounts of an alkoxyamine includes, however, the following difficulties:

1. The isolation and purification of the intermediates by filtration or distillation is laborious and expensive. The total yield over all steps is unsatisfactory.
2. The polar or protic solvents normally used in alkylation (see EP-A 23 560 and 121 701) interfere in the following hydrolysis and must therefore be removed completely from the O-substituted oximes and recycled. When using nonpolar aprotic solvents such as toluene, xylene or cyclohexane in step 2, according to EP-A 158 159 a large excess of oxime has to be employed, which then has to be isolated again in a roundabout way.

There is therefore a need for a simple process in which the disadvantages outlined above are avoided. Associated with the realization of these requirements would be a lower outlay in terms of apparatus, a more favorable total yield and thus a higher economy.

A process for preparing O-substituted hydroxylammonium salts of the formula I has now been found, which comprises reacting in an integrated process, without isolation of intermediates a) acetone with hydroxylammonium sulfate and sodium hydroxide solution to give the acetone oxime of the formula II

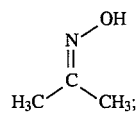

b) treating the solution of acetone oxime thus obtained with sodium hydroxide solution and completely removing water, c) reacting the suspension thus obtained of the acetone oxime Na salt III

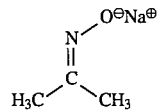

with alkylating agents of the formula IV $$RY \qquad \qquad IV$$

where R has the meaning mentioned in formula I and Y is a nucleofugic leaving group, at from 0.5 to 15 bar and at up to 140° C. to give acetone oxime ethers of the formula V

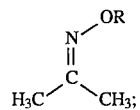

d) cleaving the acetone oxime ethers with acids HX to give the products I, a homogeneous, nonpolar aprotic solvent being used in all process steps a) to d).

In the process according to the invention, all reaction steps are performed in a one-pot process in the presence of an organic nonprotic solvent, which is particularly suitable as an entraining agent for the removal of water of reaction.

Particularly advantageously, suitable hydrocarbons are aromatic, aliphatic and cycloaliphatic hydrocarbons such as benzene, toluene, o-, m- or p-xylene, hexane or cyclohexane. Toluene is particularly preferred.

The individual steps of the entire process are summarized in the following reaction scheme:

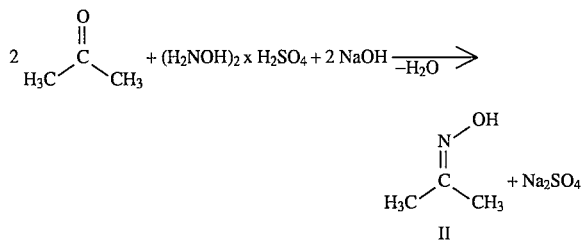

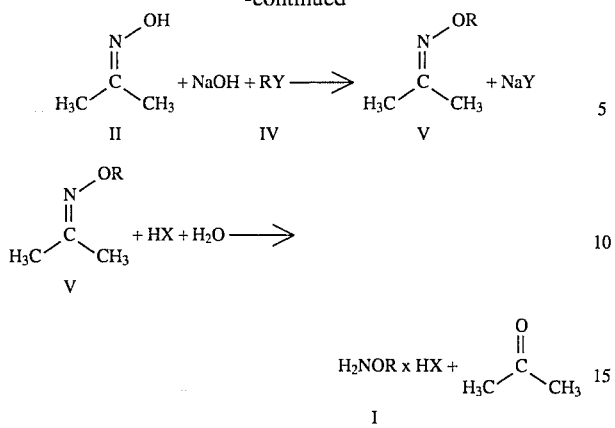

First, hydroxylammonium sulfate is reacted with acetone and sodium hydroxide solution to give the acetone oxime II, this is treated with sodium hydroxide solution, the water of reaction is removed azeotropically and the mixture is alkylated to give the acetone oxime ether V. This is cleaved without further purification using acids HX to give the desired ammonium salts I.

The first reaction step is carried out in aqueous medium in a manner known per se and the oxime II is then extracted using the solvent. Without further purification, the product solution is treated with approximately equimolar amounts of sodium hydroxide solution, eg. from 0.8 to 1.2 mol, in particular 1.0 mol, based on II, of sodium hydroxide solution such that the sodium salt III is formed, toluene/water is removed azeotropically and the toluene suspension of the sodium salt of acetone oxime is reacted with the alkylating agent RY. The alkylating agents used can advantageously be $C_1$-$C_6$-alkyl or $C_2$-$C_6$-alkenyl halides, in particular chlorides or bromides. In addition, dialkyl sulfates such as dimethyl sulfate are also suitable. To prepare ammonium salts where R=methyl, methyl chloride is preferably used as an alkylating agent.

The alkylating agent can be used according to the quantitative details described in the prior art. An excess of oxime salts relative to the alkylating agent is not necessary, however, in the process according to the invention.

The alkylation to give the acetone oxime ether V is carried out at up to 140° C., eg. from 20° to 140° C., in particular from 30° to 80° C. and at from 0.5 to 15 bar, in particular from 1 to 4 bar.

If appropriate, the alkylation can be carried out with addition of catalytic amounts of phase-transfer catalysts such as tetraalkylammonium halides or quaternary phosphonium salts which have a reaction-accelerating effect. Examples of such salts are tetrabutylammonium bromide, benzyltrimethylammoniumchloride or tetrabutylphosphonium bromide.

After aqueous extraction, the oxime ether V is cleaved directly in the organic solvent, eg. toluene, using concentrated aqueous acids of HBr or, in particular, hydrochloric acid, a mixture of acetone, the solvent and dilute HX simultaneously being removed by distillation. At the end of the reaction, the product $H_2NOR \times HX$ remains dissolved in water and can be directly further employed for subsequent reactions or isolated using customary methods.

Alternatively, the oxime ether V can be extracted from toluene solution using concentrated acid, eg. conc. hydrochloric acid, and then cleaved by heating with removal of acetone by distillation.

In the process according to the invention ammonium salts I are prepared where R=$C_1$-$C_6$-alkyl or $C_2$-$C_6$-alkenyl, each of which may be halogen-substituted. On account of the further processing to give biologically active compounds, $C_1$-$C_4$-alkyl and $C_2$-$C_4$-alkenyl radicals in particular may be halogen-substituted, eg. substituted from 1 to 3 times by fluorine, chlorine or bromine and R=methyl is especially preferred.

The following example illustrates the process claimed. The total yield achieved is surprisingly high, and the experimental procedure is significantly simpler than the steps in the stepwise preparation of the intermediates.

EXAMPLES

Preparation of methoxyamine hydrochloride without isolation of intermediates

Example 1

980 ml of water, 390 g of toluene, 328 g of hydroxylammonium sulfate, 320 g of 50% strength sodium hydroxide solution and 232 g of acetone are stirred for about 1 h at pH 5. The aqueous phase is extracted a further 2 times using 460 ml of toluene and the toluene extracts are added to the toluene phase. After addition of 320 g of conc. NaOH, 250 g of water are removed. The crystal mash obtained is treated with 210 g of methyl chloride at 50° C. under a pressure of 2 bar and the mixture is vigorously stirred for 5 h at 50° C. After extraction with 800 g of water, the toluene phase is treated with 592 g of conc. hydrochloric acid and toluene/acetone/hydrochloric acid is distilled off under reflux. After 8 hours, the mixture is cooled and the toluene phase is separated off. The aqueous phase contains 238 g of methoxyamine hydrochloride=71% yield based on acetone (over all steps).

Example 2

980 ml of water, 390 g of toluene, 328 g of hydroxylammonium sulfate, 320 g of 50% strength sodium hydroxide solution and 232 g of acetone are stirred at pH 5 for about 1 h. The aqueous phase is extracted a further 2 times using 460 ml of toluene each time and the toluene extracts are added to the toluene phase. After addition of 320 g of conc. NaOH, 250 g of water are removed. The crystal mash obtained is treated with 1.5 g of tetrabutylammonium bromide and treated with 210 g of methyl chloride for 5 h at 50° C. under a maximum pressure of 2 bar and the mixture is intensively stirred for 5 h at 50° C. After extraction with 800 g of water, the toluene phase is extracted with 750 g of conc. hydrochloric acid and the acidic extract obtained is distilled at a maximum still temperature of 100° C. After complete removal of acetone by distillation, the residue is diluted with 400 g of water. The 30% strength solution obtained contains 230 g of methoxyamine hydrochloride=69% yield based on acetone.

Comparative examination of literature yields

The preparation of acetone oxime takes place in about 90% yield. Optimized according to EP-A 23 560, acetoxime O-methyl ether is obtainable in 62% yield. According to EP-A 591 798, cleavage to give methoxyamine hydrochloride takes place in 90% yield. After multiplication of the individual yields the total yield is only 50%.

We claim:

1. A process for preparing O-substituted hydroxylammonium salts of the formula I $H_2NOR \times HX$    I where R is a $C_1$-$C_6$-alkyl or $C_2$-$C_6$-alkenyl radical, each of which may be halogen-substituted, and X is chlorine or bromine, which comprises reacting in an integrated process, without isolation of intermediates a) acetone with hydroxylammonium sulfate and sodium hydroxide solution to give the acetone oxime of the formula II

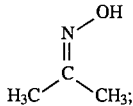

b) treating the solution of acetone oxime thus obtained with sodium hydroxide solution and completely removing water, c) reacting the suspension thus obtained of the acetone oxide Na salt III

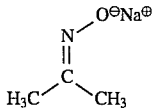

with alkylating agents of the formula IV

RY      IV where R has the meaning mentioned in formula I and Y is a nucleofugic leaving group, at from 0.5 to 15 bar and at up to 140° C., if appropriate with addition of phase-transfer catalysts, to give acetone oxime ethers of the formula V

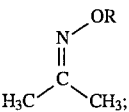

d) cleaving the acetone oxime ethers with acids HX to give the products I, a homogeneous, nonpolar aprotic solvent being used in all process steps a) to d).

2. A process as claimed in claim 1, wherein the solvent used is toluene, xylene, hexane or cyclohexane.

3. A process as claimed in claim 1, wherein the solvent used is toluene.

4. A process as claimed in claim 1, wherein the alkylating agent used is methyl chloride.

5. A process as claimed in claim 1, wherein the phase-transfer catalyst used is tetrabutylammonium bromide.

6. A process as claimed in claim 1, wherein the acid HX used is concentrated hydrochloric acid.

7. A process as claimed in claim 1, wherein the acetone oxime II is reacted with approximately equimolar amounts of sodium hydroxide solution to give the sodium salt III.

* * * * *